(12) United States Patent
Yu et al.

(10) Patent No.: US 8,968,333 B2
(45) Date of Patent: Mar. 3, 2015

(54) SUPPORT ASSEMBLY FOR ROBOTIC CATHETER SYSTEM

(75) Inventors: Alan Lau Yu, Union City, CA (US);
Daniel T. Adams, Palo Alto, CA (US);
Frederic H. Moll, San Francisco, CA (US)

(73) Assignee: Hansen Medical, Inc., Mountain View, CA (US)

( * ) Notice: Subject to any disclaimer, the term of this patent is extended or adjusted under 35 U.S.C. 154(b) by 1012 days.

(21) Appl. No.: 12/859,198

(22) Filed: Aug. 18, 2010

(65) Prior Publication Data
US 2010/0308195 A1 Dec. 9, 2010

Related U.S. Application Data

(63) Continuation of application No. 11/173,812, filed on Jul. 1, 2005, now Pat. No. 7,789,874.

(60) Provisional application No. 60/677,580, filed on May 3, 2005, provisional application No. 60/678,097, filed on May 4, 2005.

(51) Int. Cl.
*A61B 19/00* (2006.01)

(52) U.S. Cl.
CPC ........... *A61B 19/26* (2013.01); *A61B 2019/265* (2013.01); *A61B 2019/266* (2013.01)
USPC .............................. 606/130; 606/1; 248/349.1

(58) Field of Classification Search
CPC ........... A61B 2017/00234; A61B 2017/00367; A61B 2017/00371; A61B 2017/00389; A61B 19/2203
USPC ........ 606/1, 7–16, 32–50, 130; 600/101–115, 600/128–131; 248/346.01, 349.1, 521–527
See application file for complete search history.

(56) References Cited

U.S. PATENT DOCUMENTS 4,960,276 A * 10/1990 Feuer et al. ..................... 482/70
5,104,103 A    4/1992 Auchinleck et al.
(Continued)

FOREIGN PATENT DOCUMENTS

DE    2311257    9/1974
DE    19521060   12/1996
(Continued)

OTHER PUBLICATIONS

PCT International Search Report and the Written Opinion for PCT/US2005/007108, Applicant Hansen Medical, Inc., Forms PCT/ISA/210, 220, and 237 dated Jun. 26, 2005 (15 pages).
(Continued)

*Primary Examiner* — Ahmed Farah
(74) *Attorney, Agent, or Firm* — Scott M. Smith; Dorsey & Whitney LLP

(57) ABSTRACT

A support assembly for supporting a remotely-controlled instrument driver, including a first member, a second member for supporting the instrument driver, and an interface assembly for allowing the second member to rotate relative to the first member about a first axis, and for allowing the second member to rotate relative to the first member about a second axis that forms an angle relative to the first axis, wherein the interface assembly comprises a ball that is rotatable relative to the first member, and a shaft extending through the ball, the shaft configured for coupling to the second member.

11 Claims, 14 Drawing Sheets

(56) References Cited

U.S. PATENT DOCUMENTS

| | | |
|---|---|---|
| 6,106,510 A | 8/2000 | Lunn et al. |
| 6,530,913 B1 | 3/2003 | Giba et al. |
| 6,852,261 B2 | 2/2005 | Benjamin |
| 6,905,460 B2 * | 6/2005 | Wang et al. .................. 600/102 |
| 7,037,290 B2 | 5/2006 | Gardeski et al. |
| 7,214,230 B2 | 5/2007 | Brock et al. |
| 7,276,044 B2 | 10/2007 | Ferry et al. |
| 2003/0135204 A1 * | 7/2003 | Lee et al. .................. 606/1 |
| 2003/0158463 A1 * | 8/2003 | Julian et al. .................. 600/104 |
| 2003/0191455 A1 * | 10/2003 | Sanchez et al. .................. 606/1 |
| 2006/0293643 A1 * | 12/2006 | Wallace et al. .................. 606/1 |
| 2008/0167750 A1 | 7/2008 | Stahler et al. |
| 2008/0218770 A1 | 9/2008 | Moll et al. |
| 2008/0245946 A1 | 10/2008 | Yu |
| 2008/0275367 A1 | 11/2008 | Barbagli et al. |
| 2009/0036900 A1 | 2/2009 | Moll |
| 2009/0138025 A1 | 5/2009 | Stahler et al. |
| 2010/0204714 A1 * | 8/2010 | Shoham .................. 606/130 |

FOREIGN PATENT DOCUMENTS

| | | |
|---|---|---|
| EP | 1520548 | 4/2005 |
| FR | 2339936 | 8/1997 |
| WO | 97/44089 | 11/1997 |
| WO | 03/077769 | 9/2003 |
| WO | 2005/087128 | 9/2005 |

OTHER PUBLICATIONS

PCT International Search Report and the Written Opinion for PCT/US2006/025854, Applicant Hansen Medical, Inc., Forms PCT/ISA/210, 220, and 237 dated Nov. 22, 2006 (16 pages).

PCT International Search Report and the Written Opinion for PCT/US2006/017396, Applicant Hansen Medical, Inc., Forms PCT/ISA/210, 220, and 237 dated Jan. 23, 2007 (19 pages).

* cited by examiner

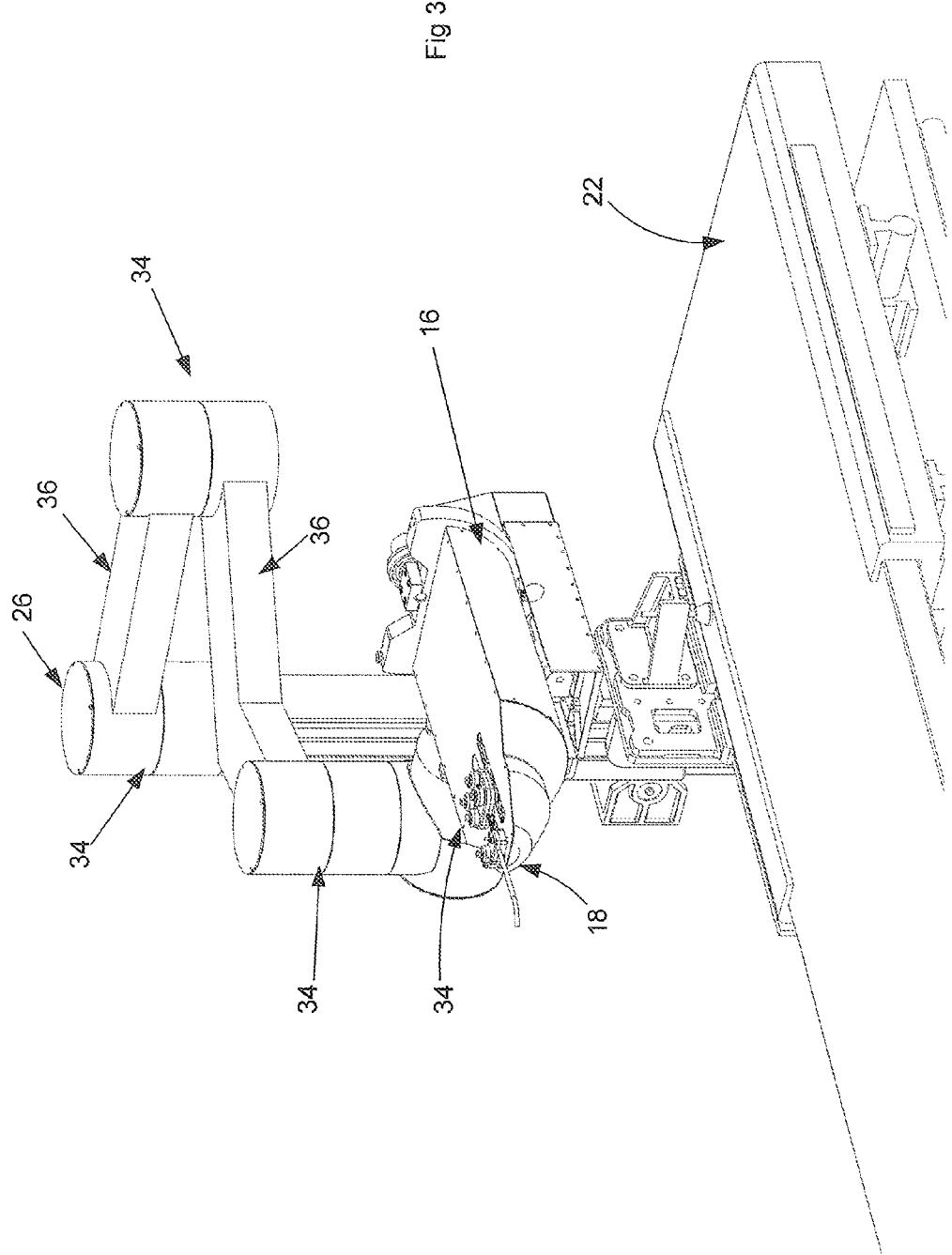

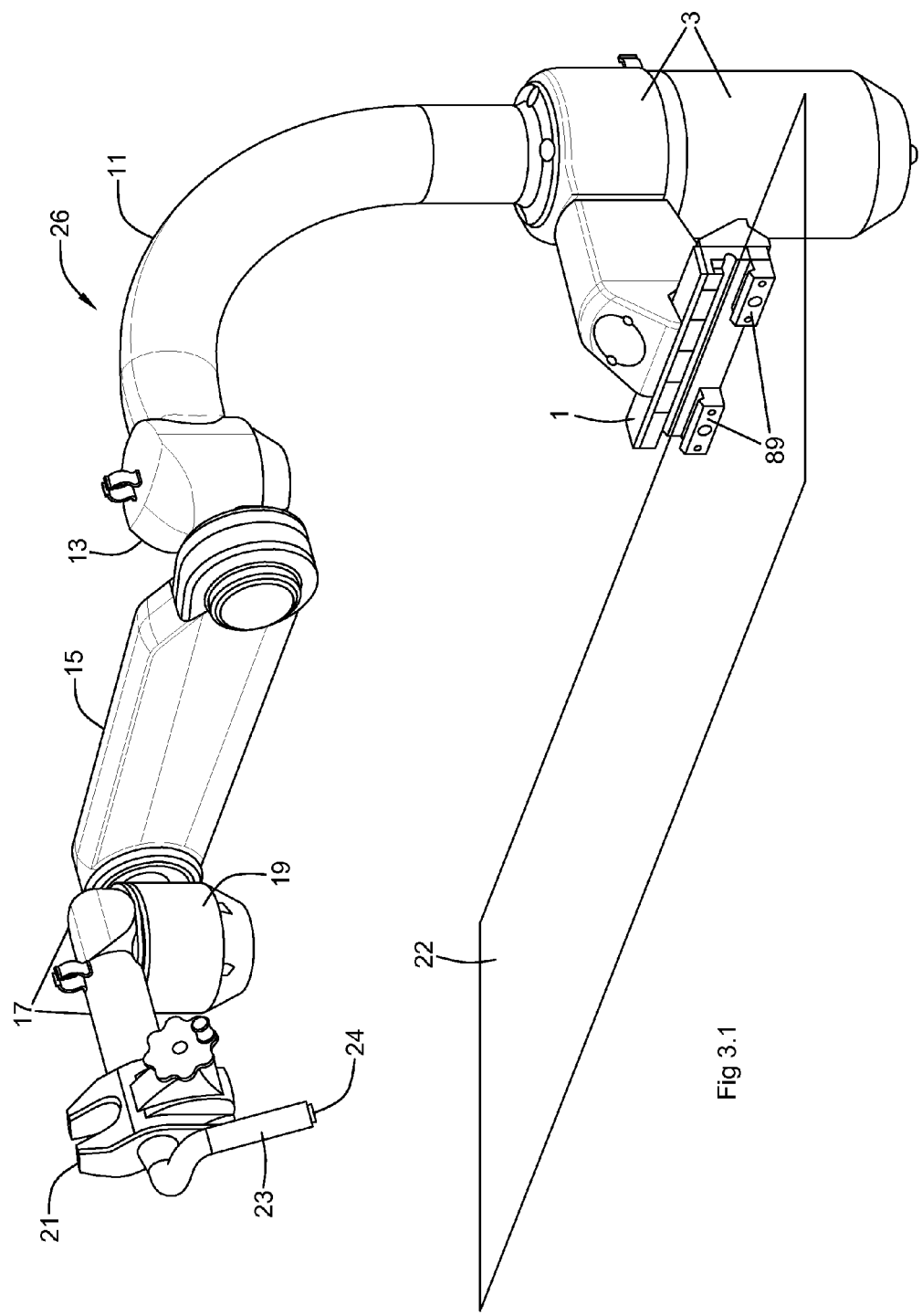
Fig 3.1

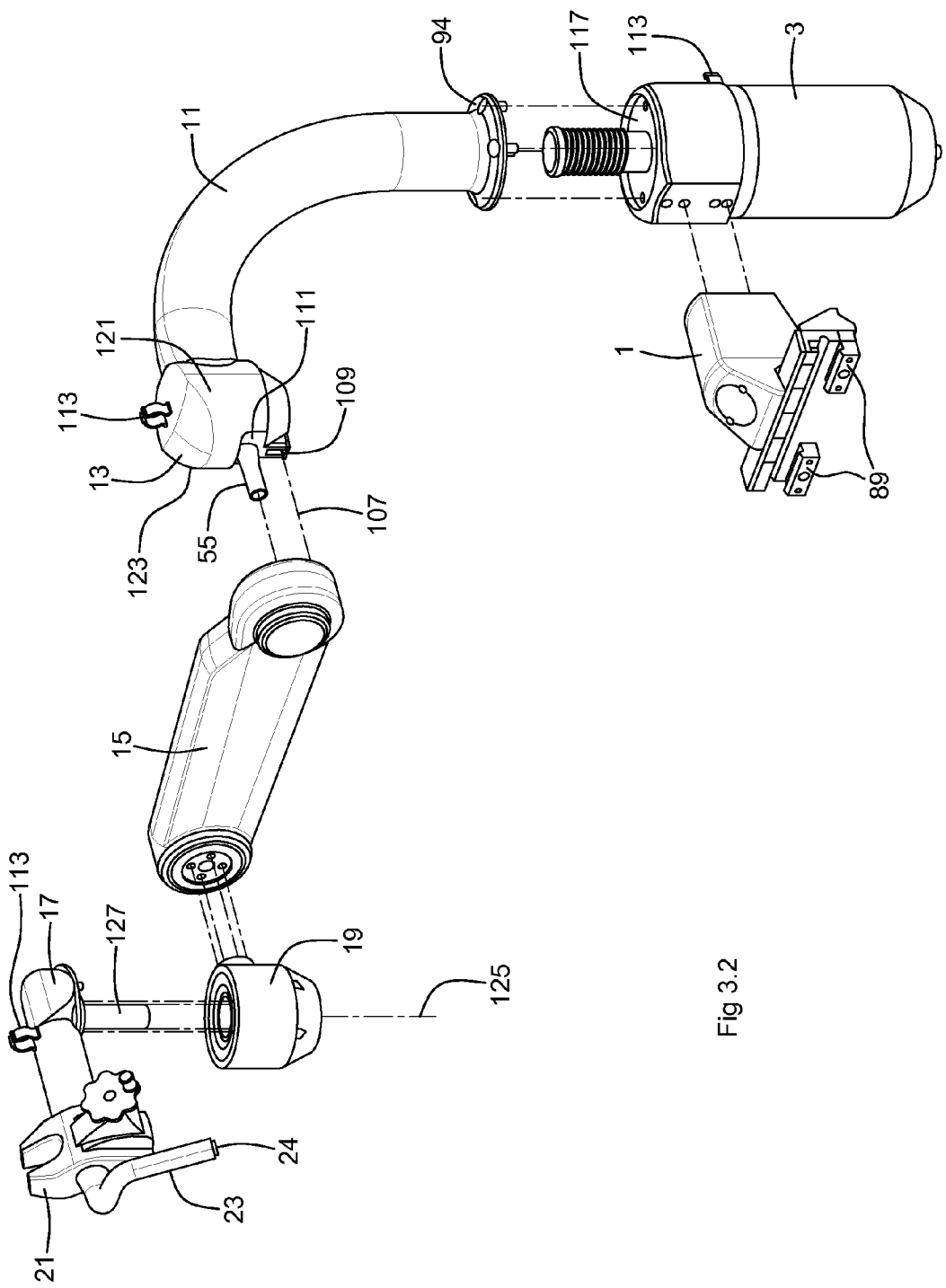
Fig 3.2

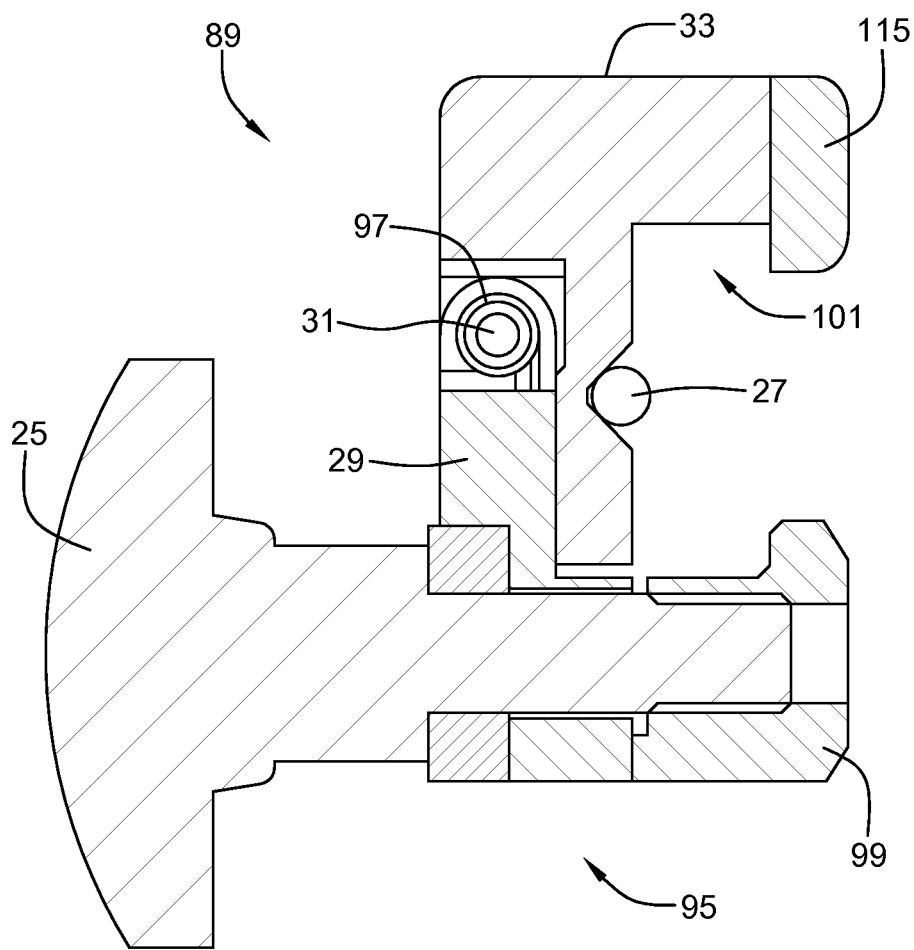
Fig 3.3

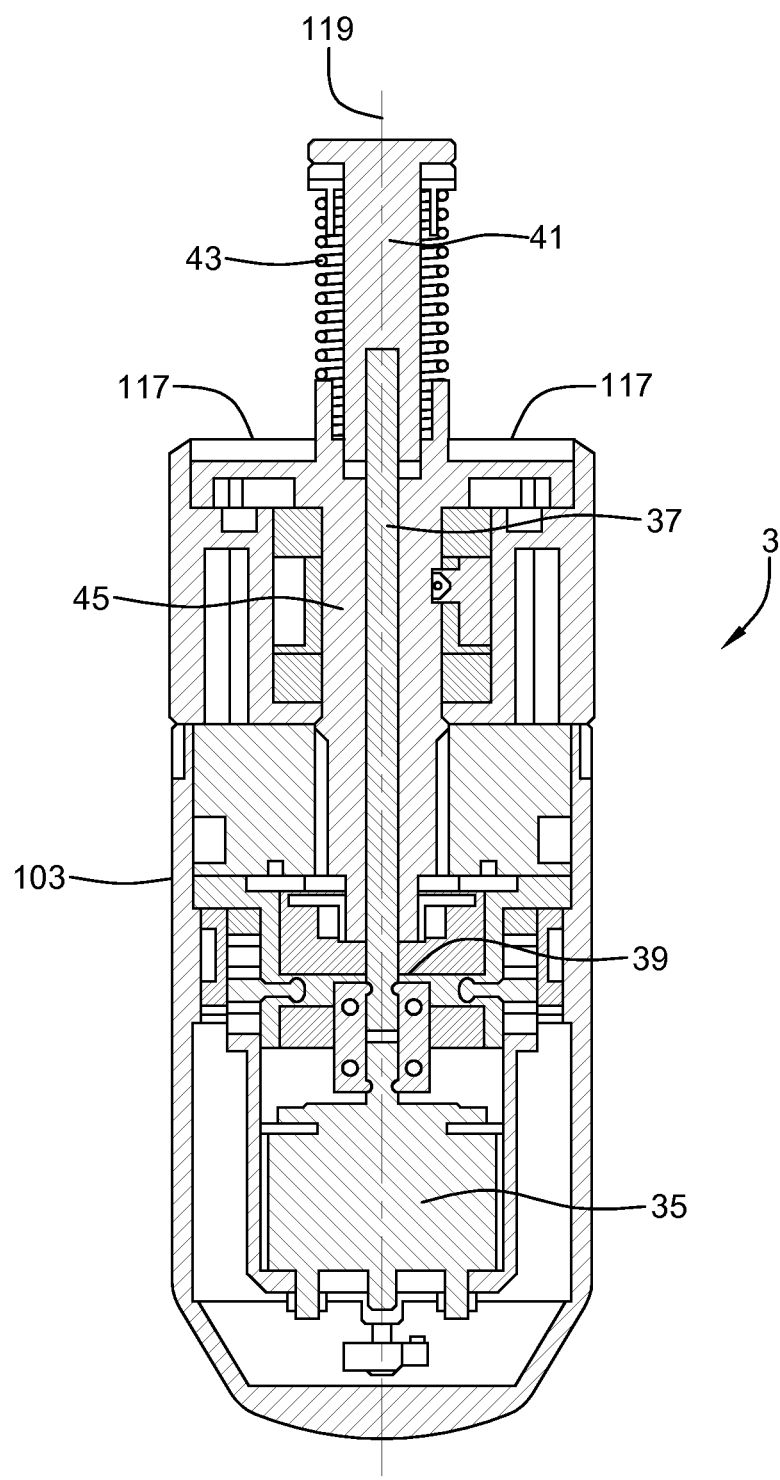
Fig 3.4

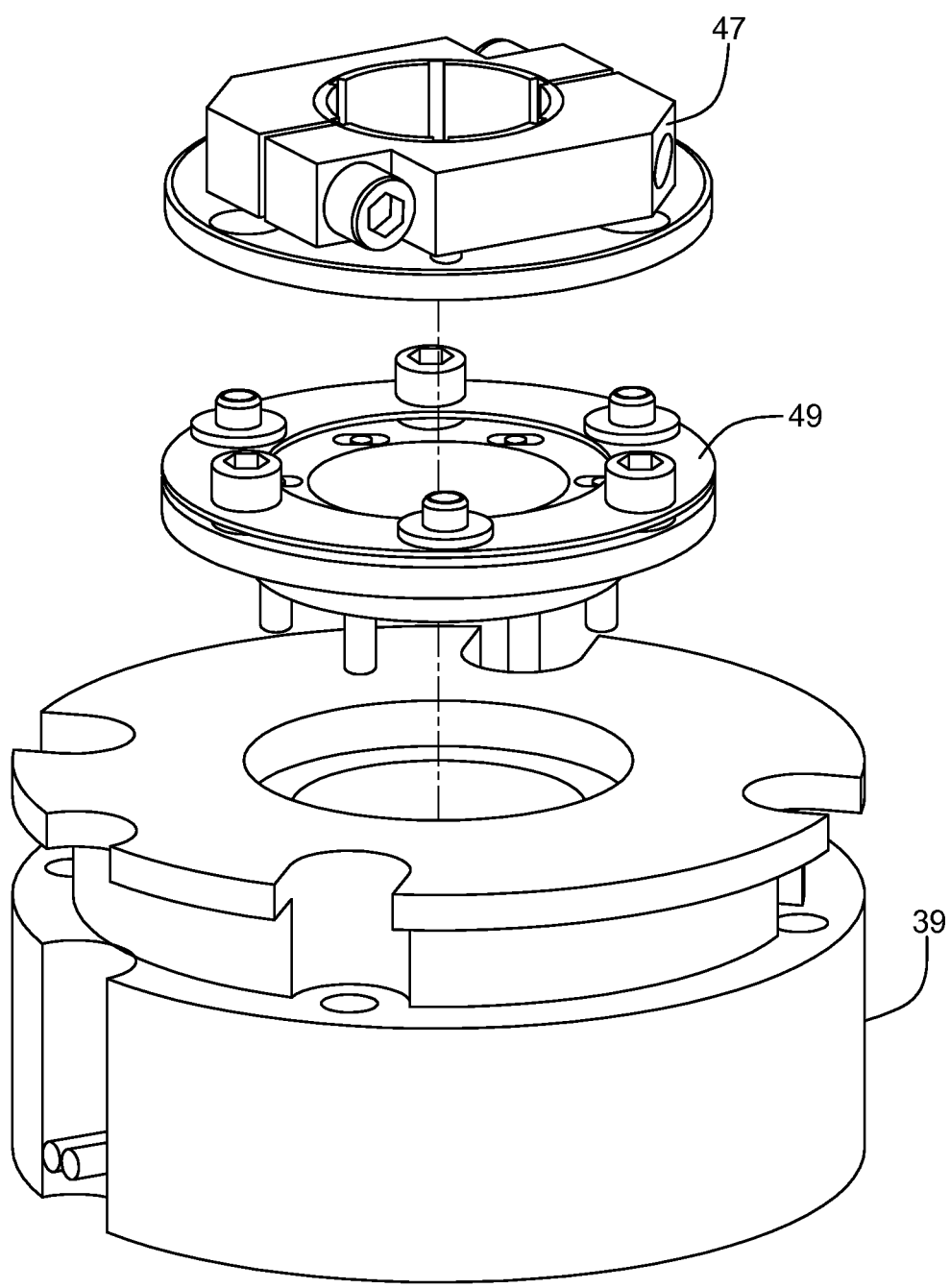
Fig 3.5

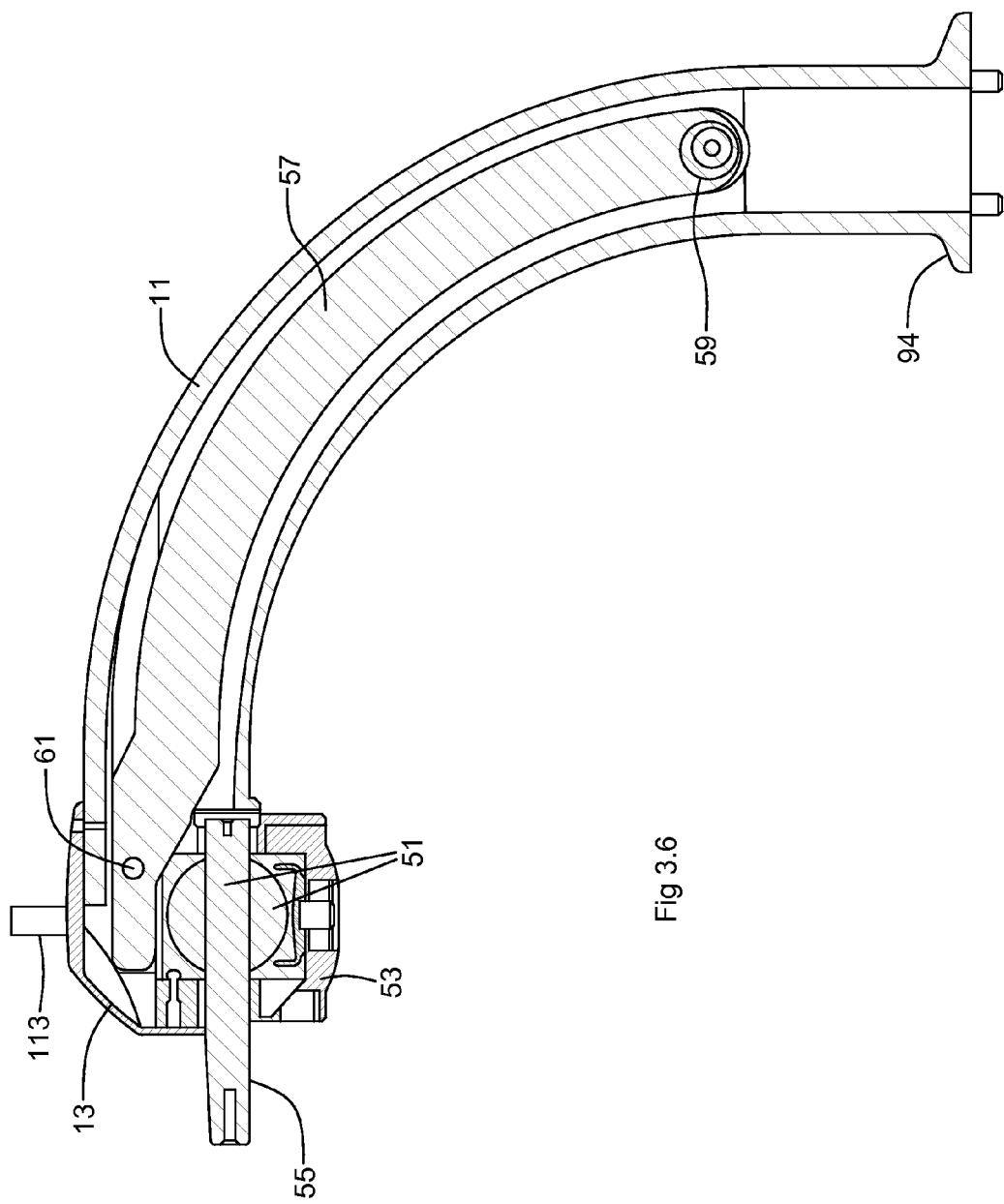
Fig 3.6

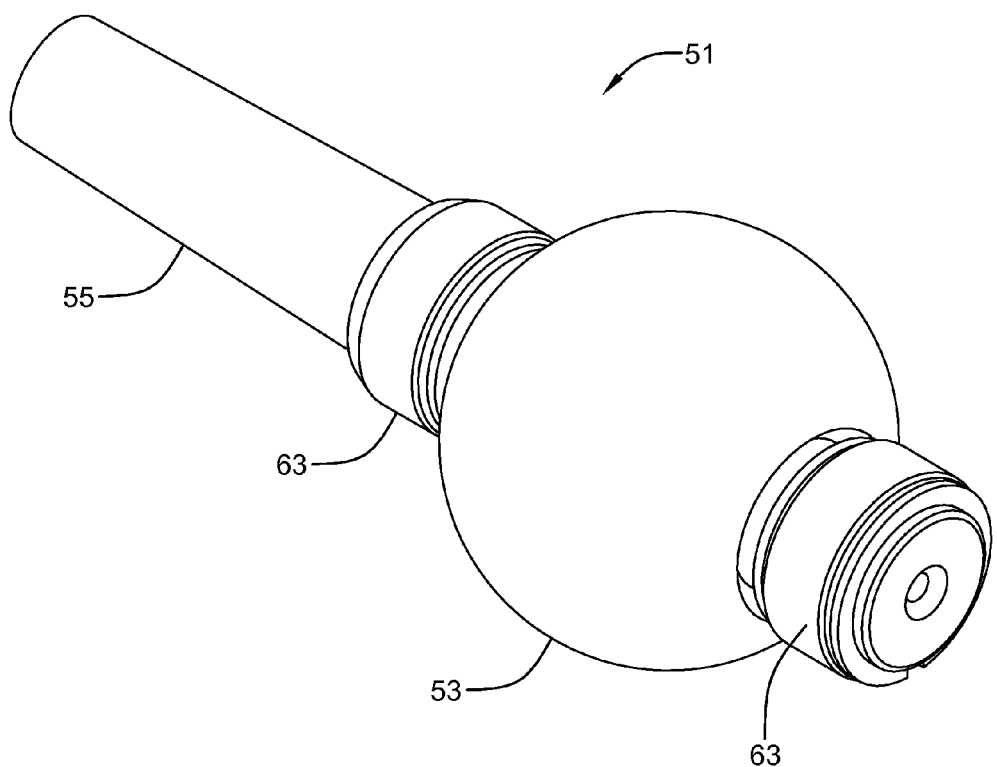
Fig 3.7

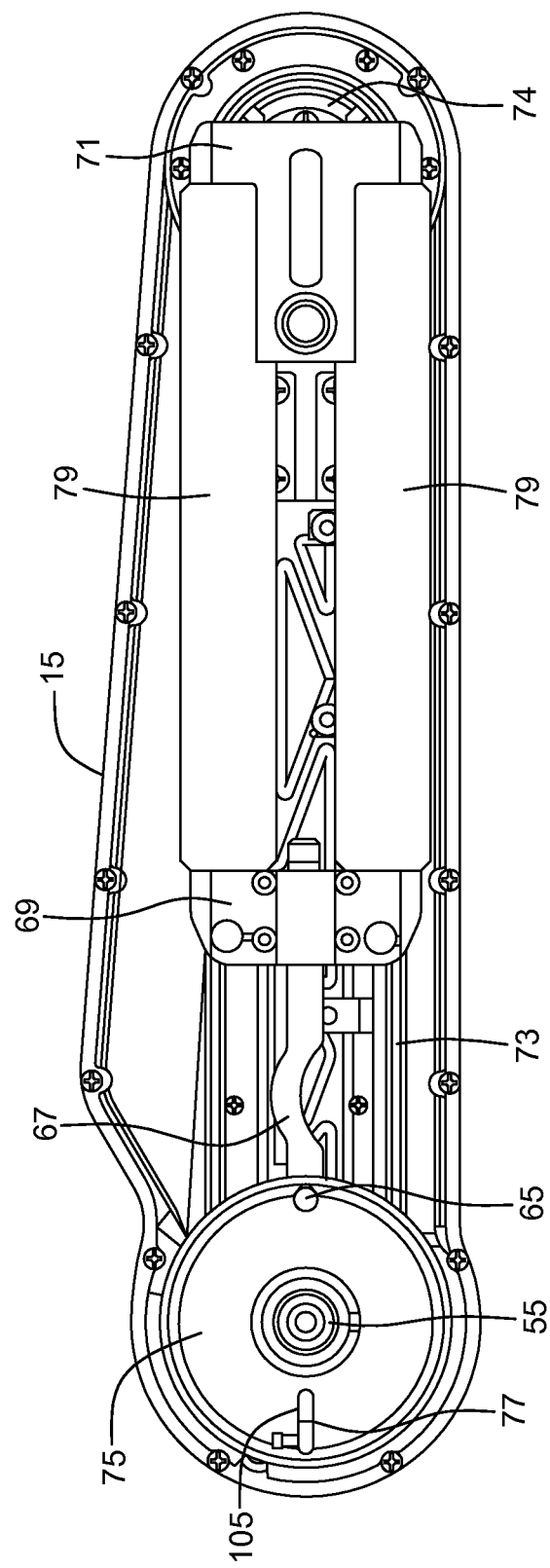
Fig 3.8

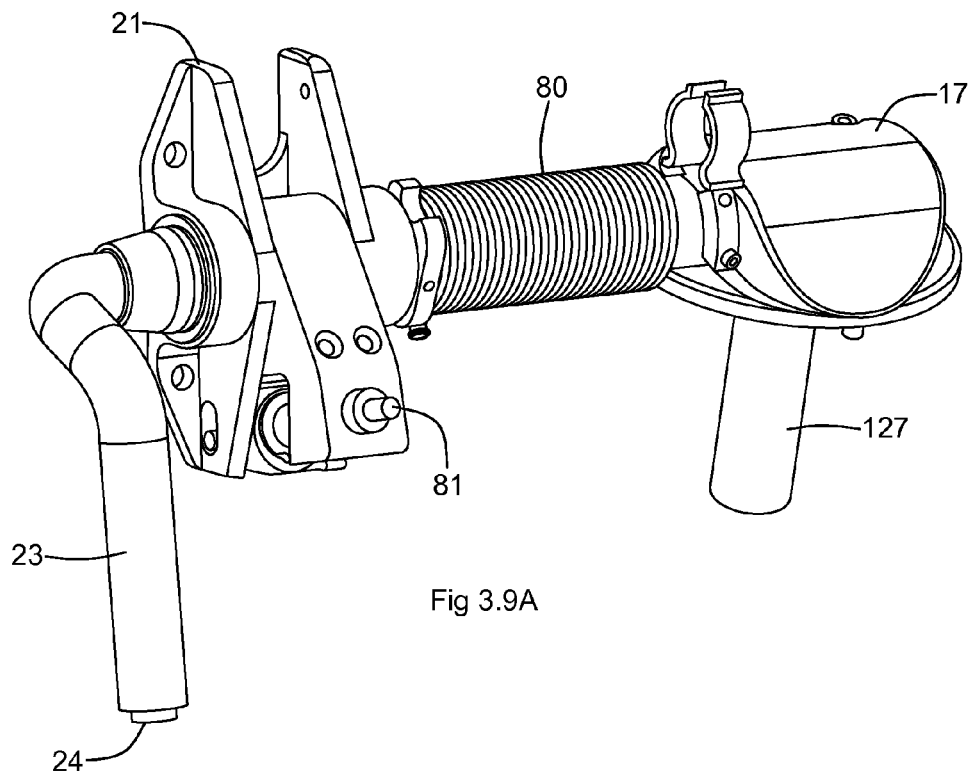
Fig 3.9A
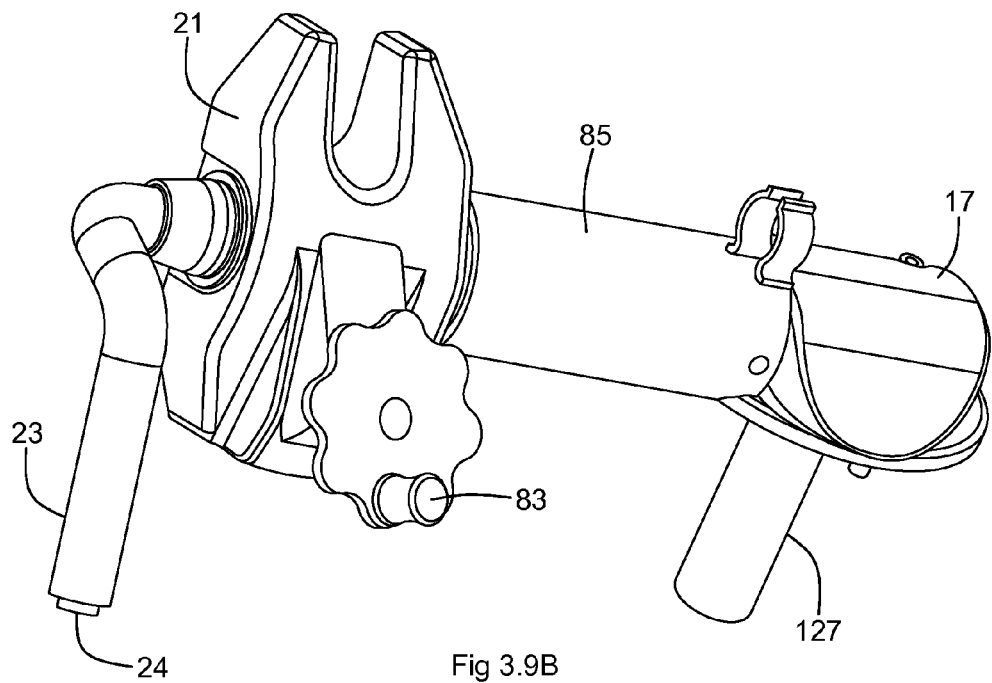
Fig 3.9B

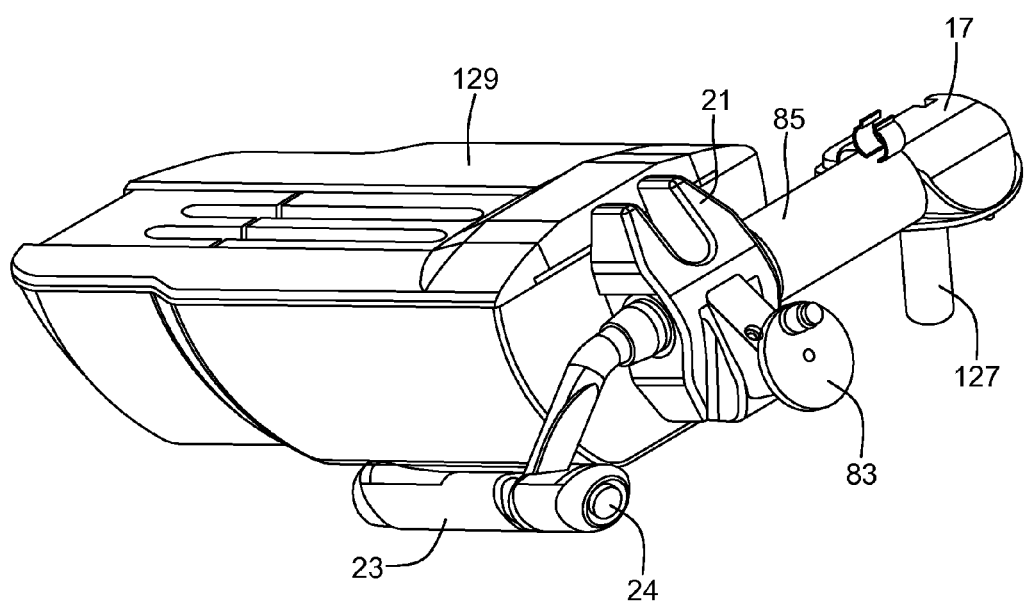
Fig 3.10A

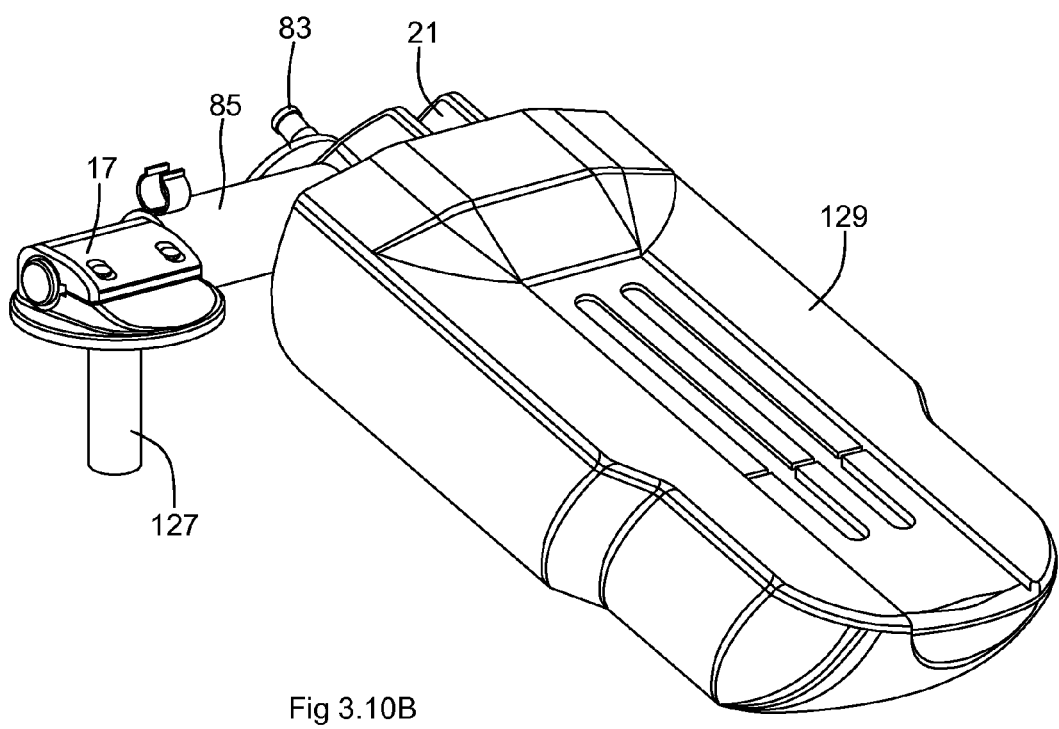
Fig 3.10B

SUPPORT ASSEMBLY FOR ROBOTIC CATHETER SYSTEM

RELATED APPLICATION DATA

The present application is a continuation of U.S. patent application Ser. No. 11/173,812, filed Jul. 1, 2005, now issued as U.S. Pat. No. 7,789,874 on Sep. 7, 2010, which claims the benefit under 35 U.S.C. §119 to U.S. provisional patent application Ser. Nos. 60/677,580, filed May 3, 2005, and 60/678,097, filed May 4, 2005, which are incorporated by reference into the present application in their entirety.

The present application is also related to U.S. patent application Ser. No. 11/073,363, filed Mar. 4, 2005, now issued as U.S. Pat. No. 7,972,298 on Jul. 5, 2011, which claims the benefit under 35 U.S.C. §119 to U.S. provisional patent application Ser. Nos. 60/550,961, filed Mar. 5, 2004, 60/553,029, filed Mar. 12, 2004, 60/600,869, filed Aug. 12, 2004, and 60/644,505, filed Jan. 13, 2005. The foregoing applications are also incorporated by reference into the present application in their entirety.

FIELD OF INVENTION

The invention relates generally to robotically controlled catheter systems, and more particularly to support arm assemblies for mounting and positioning an instrument driver to a operating table in a robotic catheter system.

BACKGROUND

Robotic catheter systems and devices are well suited for use in performing minimally invasive medical procedures, as opposed to conventional techniques wherein the patient's body cavity is open to permit the surgeon's hands access to internal organs. For example, there is a need for a highly controllable yet minimally sized system to facilitate imaging, diagnosis, and treatment of tissues which may lie deep within a patient, and which may be accessed via naturally-occurring pathways such as blood vessels or the gastrointestinal tract, or small surgically-created pathways.

SUMMARY OF THE INVENTION

In accordance with various embodiments of the invention, a support assembly is provided for supporting a remotely-controlled instrument driver relative to the patient. In one embodiment, a support assembly for supporting a remotely-controlled instrument driver, including a first member, a second member for supporting the instrument driver, and an interface assembly for allowing the second member to rotate relative to the first member about a first axis, and for allowing the second member to rotate relative to the first member about a second axis that forms an angle relative to the first axis, wherein the interface assembly comprises a ball that is rotatable relative to the first member, and a shaft extending through the ball, the shaft configured for coupling to the second member.

In one embodiment, the support assembly comprises a base removably attachable to an operating table, and an actuator assembly coupled to the base. In one embodiment, the base comprises a clamp having a clamp body portion configured to pivot relative to the base. The actuator assembly includes a rotable member and a brake configured to selectively allow rotation of the rotatable member about a first axis, which is preferably substantially perpendicular to the operating table. The actuating assembly further includes an actuator, such as, e.g., a solenoid.

A first extension member has a first end mounted to the rotatable member, such that the brake selectively allows rotation of the first extension member about the first axis. By way of non-limiting example, the brake may be configured to prevent rotation of the first extension member about the first axis unless it is electronically activated, in which case it allows such rotation. A second extension member is coupled to a second end of the first extension member via an interface assembly configured to selectively allow rotation of the second extension member about a second axis, which may be substantially parallel to the first axis, upon activation of the actuator. In one embodiment, the interface assembly is further configured to also allow rotation of the second extension member about a third axis, which is preferably substantially orthogonal to the second axis, upon activation of the actuator. In such embodiment, the second extension member may comprise a force-resisting mechanism to resist rotation of the second extension member about the third axis.

In one embodiment, the interface assembly comprises a shaft having a first end coupled to a ball joint and a second end coupled to the second extension member. A lever arm extends through the first extension member, the lever arm subjected to a biasing force to thereby retain the ball joint in a locked position, the actuator assembly configured to overcome the biasing force upon activation of the actuator, thereby allowing the ball joint to move to an unlocked position. The ball joint is preferably oriented within the interface assembly to be in an unlocked position due to gravitational force in the absence of being constrained in a locked position by the lever arm. In one embodiment, the lever arm is operatively coupled with a leveraging mechanism configured to apply a leveraged force on the ball-joint. In preferred embodiments, the levering mechanism causes the lever arm to apply a leveraged forced on the ball joint in a range between about 5:1 to about 20:1, and in one embodiment, at a ratio of about 15:1.

In various embodiments, the second extension member comprises a first end attached to the second end of the shaft, with a first sprocket rotatably attached to the first end and fixed to the first extension member, such that the first sprocket rotates in proportion to rotation of the second extension member about the third axis. A second sprocket is rotatably attached to a second end of the second extension member, with the first and second sprockets linked so that the second sprocket rotates in proportion to rotation of the first sprocket. The support assembly further comprises a support member configured for mounting and carrying the instrument driver, wherein the support member may be coupled to the second sprocket in a manner such that an instrument driver mounted to the support member remains in a substantially same orientation relative to the operating table, regardless of rotation of the second extension member relative to the interface assembly. By way of one example, a support member brake housing is fixedly attached to the second sprocket, the brake housing defining an aperture facing away from the operating table that rotatably seats the instrument driver support member. In this manner, the instrument driver support member may be selectively rotated about an axis defined by the brake housing aperture, wherein the axis remains in the same orientation relative to the operating table, regardless of rotation of the second extension member about the interface assembly.

In one embodiment, rotation of the first extension member about the first axis is prevented unless the actuating assembly brake is electronically activated, and rotation of the instrument driver support member about the support member brake aperture is prevented unless the support member brake is electronically activated. The actuator is preferably also electronically activated. Preferably, the actuating assembly brake, instrument driver support member brake, and the actuator are all activated by a common control signal. In one embodiment, the control signal is activated by depression of a button located on the instrument driver support member.

In one embodiment, an adjustable mounting interface is carried on the instrument driver support member and configured for mounting an instrument driver in a selectable pitch relative to the operating table. A biasing spring may be carried on the support member and configured to at least partially counterbalance a cantilevered load upon the instrument driver mounting interface caused by the weight of an instrument driver mounted upon it.

Other and further embodiments and aspects of the invention will become apparent upon review of the following detailed description in view of the illustrated embodiments.

BRIEF DESCRIPTION OF THE DRAWINGS

The drawings illustrate the design and utility of illustrated embodiments of the invention, in which similar elements are referred to by common reference numerals, and in which:

FIG. 3 illustrates one embodiment of a support assembly for mounting an instrument driver to an operating table;

FIG. 3.1 is a perspective isometric view of another embodiment of a support assembly for mounting an instrument driver to an operating table;

FIG. 3.2 is an exploded isometric view of the support assembly of FIG. 3.1;

FIG. 3.3 is a cut-away side sectional view of a table clamp used in the support assembly of FIG. 3.1;

FIG. 3.4 is a cut-away side sectional view of a solenoid and brake unit used in the support assembly of FIG. 3.1;

FIG. 3.5 is an exploded isometric view of a brake assembly used in the solenoid and brake unit of FIG. 3.4;

FIG. 3.6 is a cut-away side sectional view of an arcuate vertical extension member used in the support assembly of FIG. 3.1;

FIG. 3.7 is a perspective isometric view of a ball/shaft interface used to movably a horizontal extension member to the arcuate extension member of FIG. 3.6;

FIG. 3.8 is a cut-away side sectional view of the horizontal extension member in the support assembly of FIG. 3.1;

FIG. 3.9A is partially cut-away, perspective isometric view of an instrument driver mounting shaft and handle assembly used in the support assembly of FIG. 3.1;

FIG. 3.9B is a perspective isometric view of the instrument driver mounting shaft and handle assembly of FIG. 3.9A;

FIG. 3.10A is a perspective isometric view of an instrument driver as mounted to one embodiment of a support assembly; and FIG. 3.10B is a reverse perspective isometric view of the structures depicted in FIG. 3.10A.

DETAILED DESCRIPTION OF THE ILLUSTRATED EMBODIMENTS

Figure 1:
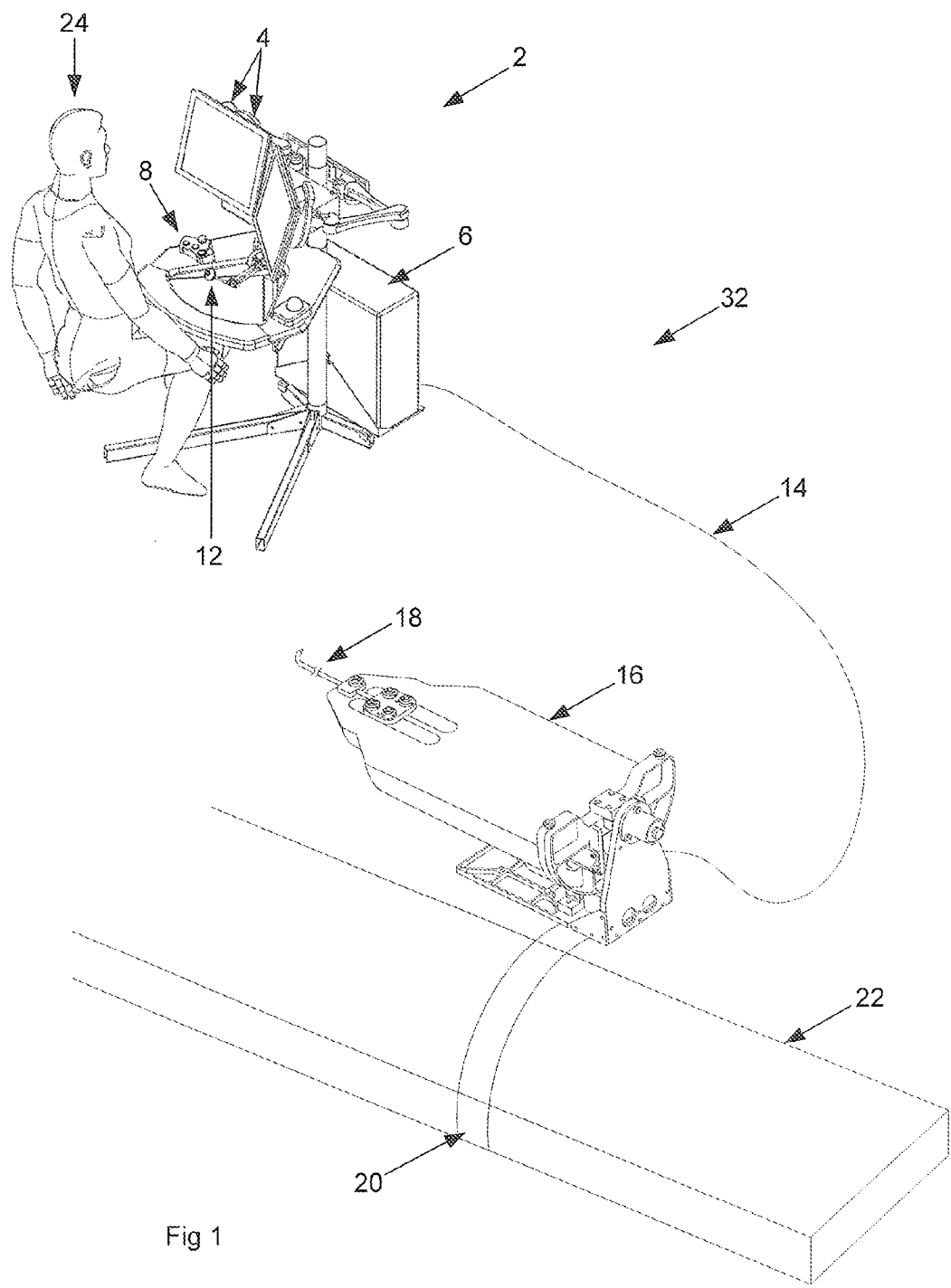
FIG. 1 illustrates a robotic catheter system in accordance with one embodiment.

Referring to FIG. 1, one embodiment of a robotic catheter system 32, includes an operator control station 2 located remotely from an operating table 22, to which a instrument driver 16 and instrument 18 are coupled by a instrument driver mounting brace 20. A communication link 14 transfers signals between the operator control station 2 and instrument driver 16. The instrument driver mounting brace 20 of the depicted embodiment is a relatively simple, arcuate-shaped structural member configured to position the instrument driver 16 above a patient (not shown) lying on the table 22.

Figure 2:
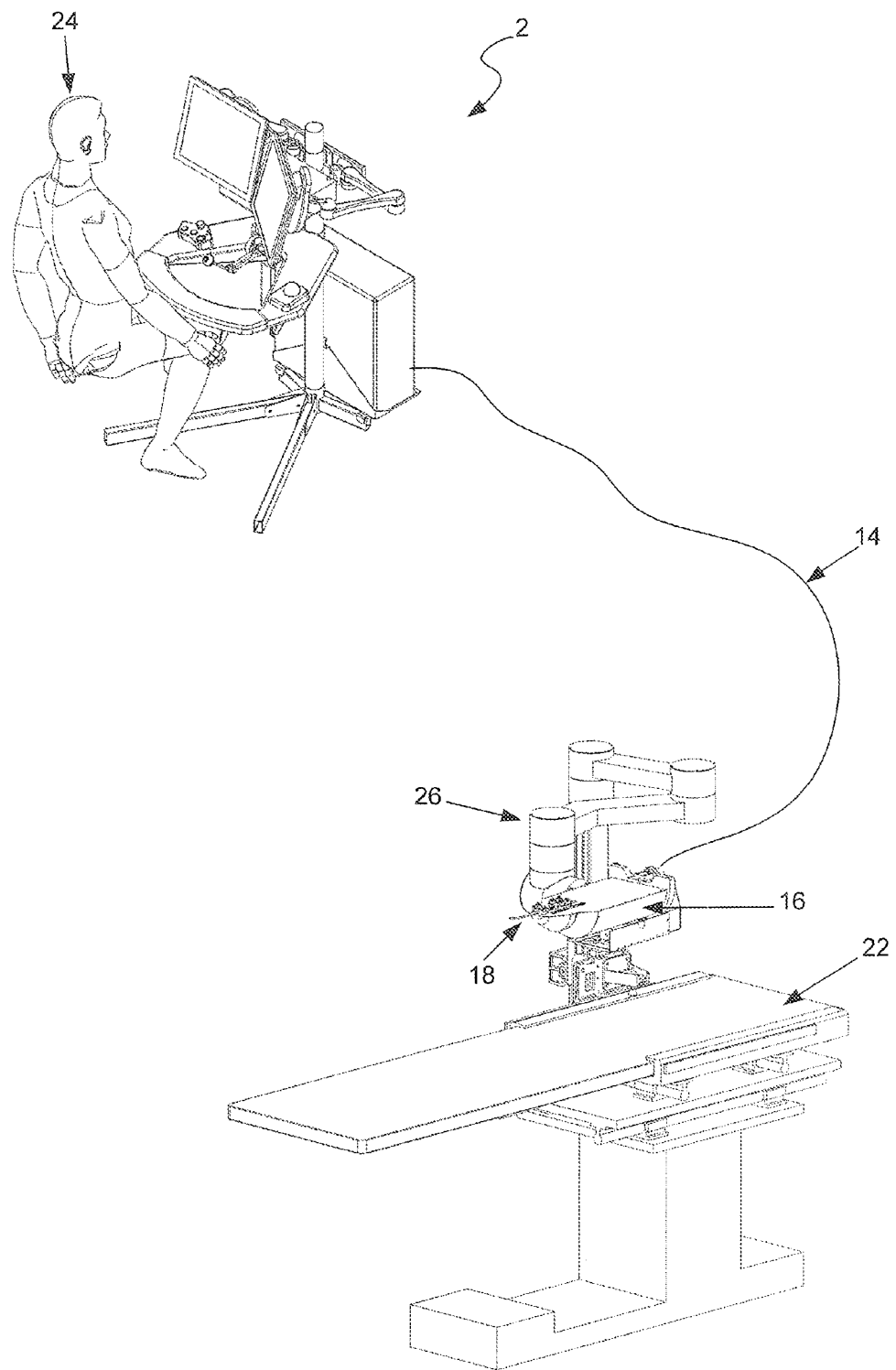
FIG. 2 illustrates a robotic catheter system in accordance with another embodiment.

In FIG. 2, another embodiment of a robotic catheter system is depicted, wherein the arcuate-shaped member 2 is replaced by a movable support-arm assembly 26. The support assembly 26 is configured to movably support the instrument driver 16 above the operating table 22 in order to position the instrument driver 16 for convenient access into desired locations in a patient (not shown). The support assembly 26 in FIG. 2 is also configured to lock the instrument driver 16 into position once it is positioned.

FIG. 3 provides a closer view of the support assembly 26 depicted in the embodiment of FIG. 2. The support assembly 26 comprises a series of rigid links 36 coupled by electronically braked joints 34. The joints 34 allow motion of the links 36 when energized by a control system (not shown), but otherwise prevent motion of the links. The control system may be activated by a switch (e.g., a footswitch), or computer interface. In another embodiment, the rigid links 36 may be coupled by mechanically lockable joints, which may be locked and unlocked manually using, for example, locking pins, screws, or clamps. The rigid links 36 preferably comprise a light but strong material, such as high-gage aluminum, shaped to withstand the stresses and strains associated with precisely maintaining a three-dimensional position of the approximately ten pound weight of a typical embodiment of the instrument driver 16 once the position of the link 36 is fixed.

FIGS. 3.1-3.10B depict another embodiment of the support assembly, also designated by reference no. 26. Referring to FIGS. 3.1 and 3.2, in this embodiment, a mechanical operating table interface 1 includes a pair of clamp members 89 to removably attach the support assembly 26 to the operating table 22 (shown in phantom outline). As explained in greater detail in conjunction with FIG. 3.3, the clamp members 89 include a lower clamp toe configured to pivot outwards for ease in engaging a rail (not shown) on an edge of the operating table 22.

The main body of the mechanical interface 1 is fixed to the housing of a solenoid and brake unit 3. A proximal base of an arcuate, vertical extension member 11 is coupled to, and selectively rotable about a central axis of, the solenoid and brake unit 3. The vertical extension member 11 bends through an angle of approximately 90°, and has a distal end rotatably coupled, via a pan-rotate interface 13, to a first end of a further extension member 15. As explained in greater detail in conjunction with FIG. 3.6, the pan-rotate interface 13 selectively allows extension member 15 to both rotate about an axis of a distal extending shaft 55 (seen in FIG. 3.2), as well as pan laterally along an arc defined by lateral movement of the shaft 55 through a pan slot 111 defined by the housing 121 of the pan-rotate interface 13 in a plane that is preferably parallel to a plane defined by the operating table.

A distal brake unit 19 is coupled to a sprocket comprising the second end of extension member 15, the sprocket being rotatably coupled to the housing of the extension member 15, as described in further detail below. The brake unit 19 is configured for selectively allowing rotation of an instrument driver support shaft 17 relative to the brake unit 19, the support shaft 17 carrying a pivotable mounting interface 21 for attaching the instrument driver (not shown). The support shaft 17 further includes a handle portion 23, which has a button 24 for electronically actuating the respective electronic brake and solenoid in unit 3, as well as the distal brake 19, to thereby allow the afore-described motions of the various components of the assembly 26. Cable holder brackets 113 are provided along the exterior of the support shaft 17, pan-rotate interface 13, and solenoid and brake unit 3, respectively, for attaching a power/control cable from the instrument driver (not shown). One a more control cables (not seen) also extend internally within the various components of the assembly 26 from the distal end button 24 to the distal brake 19 and to the solenoid and brake unit 3.

The support assembly 26 is configured to facilitate easy positioning and repositioning of a remotely controlled instrument driver over the operating table 22. When the button 24 on the handle portion 23 is depressed, the respective electronic brakes and solenoid of the assembly 26 allow the respective interfaces to move freely relative to each other, constrained only by the interface configurations, to allow for repositioning of the handle 23 and associated instrument driver support shaft 17 relative to the operating table 22. When the button 24 is not depressed, the respective brakes prevent any further movement of the support shaft 17, wherein the support assembly 26 is configured to provide a high level of mechanical stability. In one embodiment, upon activation of the solenoid and release of the brakes, the distal brake unit 19 is configured to allow an approximately 135 degree range of motion about the rotation axis 125 of the brake unit 19, the pan-rotate interface 13 is configured to allow an approximately 140 degree range of motion rotation about the rotational axis of the shaft 55 as well as approximately 110 degrees of pan rotational motion through the plane defined by the pan slot 111, and the vertical extension member 11 is configured to allow an approximately 350 degree range of rotational motion relative to the solenoid and brake unit 3, which is configured to be coupled to an operating table.

As shown in FIG. 3.3, the mounting clamps 89 each generally comprise a fixed body portion 33 having a mating surface 101, and upper and lower clamp toe portions 115 and 99, configured for attachably coupling to a rail (not shown) disposed on an edge of the operating table 22. The lower clamp toe portion 99 is preferably fastened to the swinging clamp body portion 29, with a threaded locking member 25 used to tighten/loosen the lower clamp toe portion 99 against the rail to secure/release the clamp 89 thereto or therefrom. For ease in loading the assembly 26 onto an operating table rail, the mating surface 101 of the fixed clamp body portion 33 is indented to seat a fulcrum rod 27 that rides against a side of the rail, and the swinging clamp body portions 29 of the clamps 89 may be individually pivoted (95) about the pin member 31 to rotate away from the operating table rail (not shown) to facilitate extending the upper clamp toe member 115 onto the rail with easy access to the mating surface 101. In the depicted embodiment, the swinging clamp toe bodies 29 are spring 97 biased to rotate (95) in this manner until the mating surface 101 has been positioned against the operating table rail (not shown), subsequent to which the swinging clamp toe bodies 29 may be manually rotated about the pin 31 and wound into position interfacing with the operating table rail (not shown) with the threaded locking member 25, as depicted in FIG. 3.3.

Referring to FIG. 3.4, the solenoid and brake unit 3 comprises an outer housing 103 and an inner member 45 that is rotatably mounted within the housing 103. The inner member includes a distal facing surface 117, configured to receive a proximal mounting interface 94 of the vertical extension member 11 (See FIG. 3.2). In this manner, the extension member 11 (See FIG. 3.2) is rotatable about a longitudinal axis 119 of the solenoid and brake unit 3. A brake assembly 39 is biased to prevent rotation of member 45 (and, thus, of extension arm 11), unless electronically actuated to release the member 45. In FIG. 3.5, the brake 39 is depicted, along with a flex-disk interface 49 and a clamp 47, which couples firmly to the rotatable frame member 45. The flex-disk interface 49 allows for some axial movement between the clamp 47 and the brake 39, without significant rotational "slop" commonly associated with more conventional spline interfaces. Thus, manual rotation of the vertical arm 11 about an axis which may be substantially orthogonal to the operating table 22 (i.e., for positioning an instrument driver 16 mounted on the support shaft 17 relative to a patient positioned on the operating table 22) is selectively allowed by electronic activation of the brake 39 when the button 24 is depressed into the handle 23.

Referring back to FIG. 3.4, a top end of the unit 3 includes a plunger 41, that is biased by a set of helical springs 43 to push away from the housing 103 of the solenoid and brake unit 3, into an interior bore of the extension member 11. When a solenoid 35 located in a lower portion of the housing 103 is electronically activated, it pulls a pull-rod 37, which in turn pulls the plunger 41, in a compressive direction against the springs 43, toward the housing 103 of the solenoid and brake unit 3.

As shown in FIG. 3.6, the vertical extension member 11 has a hollow interior to accommodate an arcuate lever 57 configured to compress and lock into place the pan-rotate interface 13 when rotated counterclockwise about a pivot pin 61 within, and relative to, the vertical extension member 11 as the plunger 41 (see FIG. 3.4) is pushed upward away from the housing 103 (see FIG. 3.4) by the spring 43 load. With the plunger 41 pushed upward, the ball 53 is placed into compression between the toe 130 of the arcuate lever 57 and a contoured surface 131 coupled to the base of the pan-rotate interface 13 housing 121. The ball 53, contoured surface 131 and bearings 63 mounted upon the shaft 55 preferably are configured to place substantially all of the applied compressive load upon the ball 53 and not the bearings 63. When the plunger 41 is pulled downward by the activated solenoid 35, the load previously applied by the plunger 41 to the wheelset 59 at the end of the arcuate lever 57 is released and gravity pulls the arcuate lever 57 into clockwise rotation about the pivot pin 61, thus substantially releasing the compressive loads that lock into the place the pan-rotate interface 13 and allowing panning and rotation of the shaft 55. The pan-rotate interface 13 includes a ball 53 and shaft 55 construct (collectively indicated with ref no. as 51), that, in one embodiment, is configured to provide a 15:1 leverage ratio for loads applied by the plunger 41 at a wheel set 59 housed in the extension member 11 and coupled to the proximal end of the arcuate lever 57.

Referring to FIG. 3.7, the ball/shaft interface 51 comprises bearings 63 to facilitate stable panning rotation, as well as rotation of an associated structure about the longitudinal axis of the shaft 55. The ball 53 preferably is greased to facilitate smooth panning and rotation when not compressibly locked into position. The bearings facilitate lateral panning of the shaft member 55 about a plane formed by the pan-rotate interface 13, which causes the bearings 63 to rotate on a planar annulus about the center of the ball 53. The result is constrained motion in two different degrees of freedom: lateral panning as per the planar annulus and bearing interface, and rotation about the axis of the shaft 55. The bias force of the springs 43 on the plunger 41 extending from the solenoid housing 103 normally lock the ball/shaft interface 51 into place, preventing either panning or rotation motion at the interface. Electronic activation of the solenoid withdraws the pull-rod and, by extension, piston 41 away from the wheel set 59, thereby unloading the significant compressive forces that otherwise keep the ball 53 locked into place, allowing for panning/rotation.

Referring also back to FIG. 3.2, the shaft 55 protrudes through a horizontal slot 111 located in a distal face 123 of the housing 121 covering the pan interface 13. The slot 111 constrains the horizontal panning motion of the shaft 55 (and, by extension, the support member 15) in a plane that may be substantially parallel to the operating table within the range of motion defined by the boundaries of the slot 111.

Referring to FIG. 3.8, the shaft 55 is coupled to a proximal sprocket 75 of the horizontal extension member 15 using a conventional interference fit, such as a "number 3 Morse taper." The proximal sprocket 75 is coupled to a distal sprocket 74 by a timing chain 73, so that rotation of the shaft 55 correspondingly rotates both sprockets 74 and 75, preferably with a 1:1 ratio of rotational movement, resulting in the same rotational displacement at each of the sprockets. Rotational movement of the proximal sprocket 75, caused by fixing the relative rotational position of the proximal sprocket 75 relative to the distal face 123 of the pan rotate interface 13 housing 121 with a key member 105 fitted into key slots (77, 109) defined by the distal sprocket 75 and pan rotate interface 13 housing 121, causes rotation of a pin 65, which in turn causes tension via a linkage 67, proximal linkage base 71, and distal linkage base 69, respectively, to a set of gas tension springs 79 configured to constrain the rotational motion of the sprockets 74 and 75 (and, thus, of the shaft 55). The position (107) of the key member 105 is depicted in FIG. 3.2. Given this configuration, with the solenoid 35 activated and the pan rotate interface 13 free to move, the timing chain 73 and sprocket 74/75 configuration within the horizontal extension member 15 is configured to maintain the relative planar positioning of the most distal hardware of the system relative to the plane of the operating table. This is important because a robotic catheter driver (not shown; see FIGS. 3.10A and 3.10B, for example) may be mounted upon the instrument driver interface 21 and pulled around by the handle 23, with the solenoid activated and the brakes released, to rotate about the rotational axis 125 of the distal brake unit 19, to rotate about the axis 119 of the rotatable frame member 45 within the solenoid and brake unit housing 3, to rotate and pan about the pan-rotate interface 13 via connectivity of the horizontal extension member 15, all simultaneously, without substantially changing the planar orientation of the instrument driver interface 21 relative to the plane of the operating table (not shown). In other words, the axis of rotation 125 of the proximal extension 127 of the instrument driver support shaft 17 may be configured to always be oriented perpendicular to the plane of the operating table, by virtue of the timing chain and sprocket interfacing of the extension member 15. When electronically activated, the brake 19 allows rotational movement of the of the support shaft 17 about an axis of the proximal extension 127. When the brake is not electronically activated, such rotational movement of the support shaft 17 is prevented.

Referring to FIGS. 3.9A and 3.9B, the instrument driver support shaft 17 comprises an instrument driver mounting interface 21, and a biasing spring 80 configured to at least partially counterbalance the cantilevered load upon the instrument driver interface 21 caused by the weight of an instrument driver mounted upon it. The biasing spring 80 preferably is covered by a spring housing 85. A lead screw 81 is provided and configured to change the pitch of the instrument driver interface 21 relative to the support shaft 17 when a knob 83 is rotated.

Referring to FIGS. 3.10A and 3.10B, an instrument driver fitted with a cover 129 is depicted mounted to the instrument driver interface 21. The cover 129 is configured to provide an additional barrier between the instrument driver which is covers and draping, liquids, vapors, and other substances that may be encountered during a procedure. Preferably the cover 129 comprises a polymer or metal material and is made with processes such as stereolithography, injection molding, or machining. Preferably the cover 129 may be snapped or fastened into place around the instrument driver with simple recessed screws, bolts, or other fasteners. Similar covers may be configured to cover instrument bases. As depicted in FIGS. 3.10A and 3.10B, the cantilevered mass of the covered instrument driver 129 creates a moment. Torsional loads associated with such moment are counteracted by the spring (not shown in FIGS. 3.10A and 3.10B—see FIG. 3.9A (80)) housed within the housing 85. This counteraction is configured to prevent binding of the knob 83 actuated lead screw 81 pitch control of the instrument driver interface 21.

In summary, a support assembly 26, or support structure, is configured to allow for easy repositioning of an instrument driver or other device relative to an operating table when an actuation button is depressed, thereby activating a solenoid and releasing two electronic brakes. The position of an instrument driver then may be easily fine-tuned, for example, or modified quickly and substantially to remove the instrument driver from the immediate area of a patient on an operating table for quick medical intervention with broad physical access. Constraints limit the movement of the instrument driver relative to the operating table—i.e., a pan-rotate interface 13, a horizontal extension member 15 with a rotational position maintaining timing chain 73 for distally-coupled structures, and brake-lockable rotations about two axes of rotation (125, 119) which may be parallel and both perpendicular relative to the plane of the operating table—to provide desirable mechanics. When an actuation button is not depressed and the structures are substantially locked into position relative to each other, with the exception of manually-activated lead screw pitch adjustment of an instrument driver interface 21, the support assembly 26 is configured to provide a robust structural platform upon which an instrument driver or other device may be positioned relative to an operating table.

While multiple embodiments and variations of the many aspects of the invention have been disclosed and described herein, such disclosure is provided for purposes of illustration only.

What is claimed:

1. A support assembly for supporting an instrument driver, comprising:
   a first member coupled to a base member;
   a second member for supporting the instrument driver;
   an interface assembly comprising a joint coupling the first member to the second member, the joint configured for allowing the second member to rotate relative to the first member about a first axis, and for allowing the second member to rotate relative to the first member about a second axis; and
   an electronic brake assembly for selectively allowing rotation of the first member relative to the base member.

2. The support assembly of claim 1, wherein the interface assembly further comprises a ball that is rotatable relative to the first member, and a shaft extending through the ball, the shaft configured for coupling to the second member.

3. The support assembly of claim 2, wherein the interface assembly further comprises a first ring bearing located around the shaft on first side of the ball, and a second ring bearing located around the shaft on a second side of the ball that is opposite from the first side.

4. The support assembly of claim 2, further comprising a housing at an end of the first member, wherein the housing has a slot for accommodating a range of motion by the shaft of the interface assembly.

5. The support assembly of claim 2, further comprising a lever located within the first member for locking the interface assembly in place relative to the first member.

6. The support assembly of claim 5, further comprising a solenoid for actuating the lever in response to a control signal.

7. The support assembly of claim 5, wherein the lever comprises a toe configured to press the ball against a contoured surface.

8. The support assembly of claim 1, further comprising a base to which the first member is moveably coupled.

9. The support assembly of claim 8, wherein the base is removeably attachable to an operating table.

10. The support assembly of claim 1, wherein the second member is configured to indirectly support the instrument driver.

11. The support assembly of claim 1, wherein the joint coupling the first member to the second member is configured for allowing the second member to rotate relative to the first member about a first axis to vary an angle formed between an end portion of the first member and an end portion of the second member, and for allowing the second member to rotate relative to the first member about a second axis so that the second member moves in a plane that is perpendicular to the end portion of the first member.

* * * * *